United States Patent [19]

Yoshizuka et al.

[11] Patent Number: 4,569,931

[45] Date of Patent: Feb. 11, 1986

[54] SEBUM SECRETION ACCELERATOR

[75] Inventors: Naonobu Yoshizuka, Utsunomiya; Eijiro Takeuchi, Tochigi; Genji Imokawa, Utsunomiya, all of Japan

[73] Assignee: Kao Corporation, Tokyo, Japan

[21] Appl. No.: 627,549

[22] Filed: Jul. 3, 1984

[30] Foreign Application Priority Data

Jul. 11, 1983 [JP] Japan ................... 58-125651

[51] Int. Cl.⁴ ............................................. A61K 31/56
[52] U.S. Cl. .................................................. 514/182
[58] Field of Search ................ 260/397.2; 424/238; 514/182

[56] References Cited

U.S. PATENT DOCUMENTS 4,309,448  6/1982  Takaishi et al. ................ 260/397.2

OTHER PUBLICATIONS

Chemical Abstracts, vol. 71 (1969) Pars. 84810r and 84811s.
Chemical Abstracts, 100(4) 1983, Par. 28335v, article by Nedostup et al.

Primary Examiner—Elbert L. Roberts
Attorney, Agent, or Firm—Oblon, Fisher, Spivak, McClelland & Maier

[57] ABSTRACT

Sebum secretion accelerator composition comprising a cholesteryl ester of a branched fatty acid represented by the formula (I):

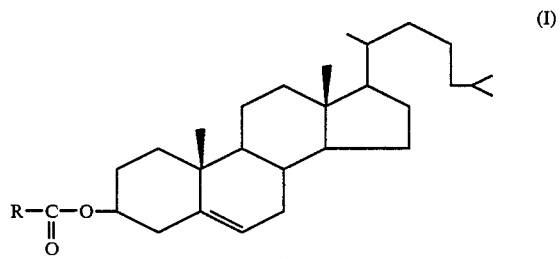

in which R represents a saturated aliphatic hydrocarbon group having from 11 to 23 carbon atoms and at least one alkyl substituent at a position between the carboxyl bond and the center of the main chain. The cholesteryl ester should be contained not smaller than 25 wt % of the total composition.

The composition according to the invention promotes sebum secretion, and is effective in keeping healthy and beautiful skin.

The composition is further advantageous in that it can be readily formed into various types of cosmetics such as lotions, creams and ointments.

9 Claims, No Drawings

SEBUM SECRETION ACCELERATOR

BACKGROUND OF THE INVENTION (i) Field of the Invention

This invention relates to sebum secretion accelerators and more particularly, to sebum secretion accelerator compositions comprising cholesteryl esters of branched fatty acids in high concentrations.

(ii) Description of the Prior Art

For the purpose of nutrition and beauty cares for skin, it is usual to apply cosmetics containing suitable lipids and water to skin. By the application, the protective film of the cosmetic is formed on the surface of the skin, thereby preventing evaporation of water and retaining a suitable degree of lipid on the skin surface. As a result, the skin is kept smooth and soft. These types of cosmetics are ordinarily employed skin lotions or cosmetics.

As is known in the art, healthy and beautiful skin is originally derived from normal secretion of sebum. With human body, the secretion of sebum is vigorous at the growing stage and is gradually reduced at the adult stage. This is more remarkable at senescence. It is generally accepted that women are less active than men with regard to the secretion of sebum. According to Greene et al, the legs are the least among parts of the body with regard to the amount of the secretion, and the amount is about one eightieth of the forehead whose amount of the secretion is the highest. In this connection, within the parts of the face, secretion in cheeks is about one third of that in the forehead. The skin at the parts where the amount of the secretion is small has the tendency toward drying [R. S. Greene et al; J. Invest. Dermatol., 54, 240 (1970)]. Accordingly, in order to exercise beauty cares for the skin of women of the middle or older ages whose amount of sebum secretion lowers, it is the most natural and favorable to cause the secretion of sebum to be promoted. However, conventional cosmetics do not serve to beautify the skin by promoting the secretion of sebum of the human body, thus not contributing to the substantial beautification of the skin. For treatment of dried and roughened skin, to accelerate the secretion from the skin brings about a great effect. Especially, the acceleration of the secretion of sebum is useful in improving efflorescence such as xerodermia, atopic dermatitis or the like and preventing exacerbation.

Known substances having the action of accelerating the sebum secretion include γ-oryzanol, pantetheine and fatty acid esters and the like. However, γ-oryzanol which is cholesterol bonded with ferulic acid through ester bonding has a melting point as high as 127° to 135° C. and cannot be added in high concentrations, thus it being difficult to make preparations. Pantetheine-fatty acid esters (Japanese Laid-open Application Nos. 54-160315 and 54-160751) are solid at room temperature with a difficulty in preparation.

SUMMARY OF THE INVENTION

In these circumstances, we made extensive studies of compounds which have the action of accelerating the sebum secretion and are ready for preparation. As a result, it was found that when used in high concentrations, cholesteryl esters of branched fatty acids of the general formula (I) which are liquid at room temperature exhibit the action of the sebum secretion. The present invention is accomplished based on the above finding.

More particularly, the present invention provides a sebum secretion accelerator composition comprising a cholesteryl ester of a branched fatty acid represented by the general formula (I)

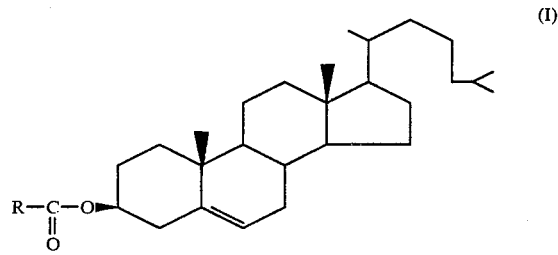

in which R represents a saturated aliphatic hydrocarbon group having from 11 to 23 carbon atoms and at least one alkyl substituent at a position between the carboxyl bond and the center of the main chain, in an amount not smaller than 25 wt % of the total composition.

DETAILED DESCRIPTION OF THE INVENTION AND PREFERRED EMBODIMENTS

The cholesteryl esters of branched fatty acids used as an essential ingredient of the composition according to the invention are compounds which are liquid at room temperature exceptionally among cholesterol derivatives synthesized by us. These esters are known to be useful as substrates for cosmetics (Japanese Laid-open Patent Application Nos. 56-65900, 56-65809, 56-167611 and 57-123108).

In these laid-open applications, it is stated that the cholesteryl esters have the hydrating property, emulsification stability, and moisture retentivity and are thus usable as substrates for cosmetics by utilizing these properties. However, the action of accelerating the sebum secretion of these esters are not stated or even suggested in these application. This is evidenced from the following fact: it is stated in these laid-open applications that preferable amounts of the cholesteryl esters compounded in cosmetics are from 0.03 to 4 wt % (hereinafter referred to simply as %). However, such small amounts as indicated above will bring about the effects of hydrating ability, emulsification stability and moisture retentivity, but little or no accelerating action of the sebum secretion develops. This action develops only when the esters are used in amount not smaller than 25% based on the total composition and is not known from these laid-open applications.

The cholesteryl esters of branched fatty acids (1) of the invention are prepared from branched fatty acids or derivatives thereof and cholesterol according to ordinary esterification techniques. More particularly, the esters may be obtained by interacting branched fatty acids and cholesterol as they are, or either of branched fatty acids or cholesterol may be first converted into more reactive derivatives thereof and then esterified with the other compound (Japanese laid-open Application No. 56-65900).

The branched fatty acids (RCOOH) which are one of the starting materials for the cholesteryl esters of branched fatty acids are those which have from 12 to 24 carbon atoms (i.e. R has carbon atoms of from 11 to 23), preferably from 14 to 20 carbon atoms (i.e. R has carbon atoms of from 13 to 19), and most preferably 18 carbon atoms. Use of branched fatty acids having smaller than 12 carbon atoms results in cholesteryl esters of branched fatty acids having poor oleophilic property. On the other hand, when the branched fatty acids used have not smaller than 24 carbon atoms, the resulting esters become poor in hydrophilic property.

The branched fatty acids should be saturated, branched fatty acids having at least one alkyl substituent at a position between the carboxyl bond and the center of the main chain. Such saturated branched fatty acids are readily obtained from starting materials used in petrochemical or fat and oil chemical industries.

Branched fatty acids obtained from starting materials of the petrochemical industry are, for example, branched fatty acids having a side chain at the α position and represented by the following formula (II)

$$R_1-\underset{R_2}{CH}-COOH \qquad (II)$$

in which $R_1$ and $R_2$ independently represent a linear or branched saturated aliphatic hydrocarbon group and the total number of carbon atoms of $R_1$ and $R_2$ ranges from 12 to 18.

The branched fatty acids of the formula (II) having the side chain at the alpha position are prepared, for example, by a process in which a linear or branched aldehyde having from 7 to 10 carbon atoms is subjected to aldol condensation to obtain an alpha-branched unsaturated aldehyde, followed by hydrogenation and oxidation to obtain a branched saturated fatty acid.

Preferable examples of the saturated branched fatty acids having the side chain at the alpha position include 5,7,7-trimethyl-2-(1,3,3-trimethylbutyl)-octanoic acid, 2-heptylundecanoic acid, 2-hexyldecanoic acid, 2-octyldodecanoic acid, 2-pentylnonanoic acid, and the like.

Examples of the saturated branched fatty acids obtained from starting materials of the oil and fat chemical industry are fatty acids of the following formula (III) having a methyl-branched chain.

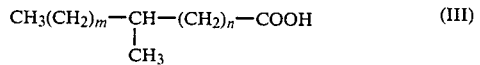
$$CH_3(CH_2)_m-\underset{CH_3}{CH}-(CH_2)_n-COOH \qquad (III)$$

in which the sum of m and n is 14 with a distribution center at m=n=7.

Such methyl-branched fatty acids are, for example, obtained as side products at the time of producing the dimer of oleic acid (J. Am. Oil Chem. Soc., 51, 522(1974)) and are hereinafter referred to as methyl-branched isostearic acid. The methyl-branched isostearic acid is commercially available, for example, in the form of an isopropyl ester thereof (Emery Co., Ltd. of U.S.A.).

Typical cholesteryl esters of branched fatty acids according to the invention have the following physical properties.

| Compounds | Properties | IR Spectrum (cm$^{-1}$) |
|---|---|---|
| Cholesteryl 5,7,7-trimethyl-2-(1,3,3-trimethylbutyl) octanoate | liquid | 2950, 2900, 2870, 1720 (C=O stretching), 1470, 1380, 1360, 1240, 1220, 1160, 1030, 1010 |
| Cholesteryl 2-heptylundecanoate | liquid | 2950, 2930, 2850, 1730 (C=O stretching), 1465, 1380, 1365, 1260, 1160, 1050 |
| Cholesteryl methyl-branched isostearate | melting point 25–30° C. | 2950, 2920, 2850, 1730 (C=O stretching), 1460, 1370, 1160, 1000 |
| Cholesteryl 2-hexyldecanoate | liquid | 2950, 2925, 2855, 1730 (C=O stretching), 1465, 1375, 1365, 1260, 1155, 1055 |
| Cholesteryl 2-octyldodecanoate | liquid | 2950, 2930, 2850, 1730 (C=O stretching), 1460, 1375, 1300–1100, 1090–930 |
| Cholesteryl 2-pentylnonanoate | liquid | 2950, 2925, 2850, 1725 (C=O stretching), 1460, 1370, 1155, 1000 |

The sebum secretion accelerator compositions of the present invention should contain 25% or more, preferably 30% or more, of the cholesteryl ester of branched fatty acid based on insoluble matters in the accelerator composition. Amounts smaller than 25% do not give satisfactory effects of accelerating the sebum secretion.

The sebum secretion accelerator composition of the invention may be prepared in various forms. In general, the composition is used in the form of lotions, creams, ointments and the like. Other ingredients which are ordinarily used in cosmetics may be further added. Such ingredients include, for example, oily substances, humectants, thickeners, preservatives, emulsifiers, medical ingredients, perfumes, emulsification stabilizers, and the like.

The accelerator composition of the invention is free of precipitation of crystals because liquid cholesteryl esters of fatty acids are contained therein. When the composition is applied to chapped or dried skin, the function of secreting the sebum is accelerated, thereby showing good effects of curing, improving or beautifying the skin.

The present invention is illustrated in more detail by way of experimental examples and examples.

Experimental Example 1

[Effect of a Cholesteryl Methyl-branched Fatty Acid Ester on the Skin of Men]

A creamy sebum secretion accelerator composition (obtained in Example 1) containing a high concentration of cholesteryl methyl-branched isostearate (as obtained in Example 3 of Japanese Laid-open Patent Application No. 56-65900, this isostearate being also used in the following experimental examples and examples) was applied onto the skin of men to determine an amount of secreted sebum prior to and after the application. More particularly, the cholesteryl-containing cream and a base cream free of the ester were each applied onto the forehead skin of healthy men at separate places thereof every day over two weeks. For comparison, a cream containing 5% γ-oryzanol was likewise applied in order to determine an amount of secreted sebum.

The measurement of the amount of secreted sebum was carried out as follows. The place or portion being treated with a cream was sufficiently defatted by application thereto with acetone/ether (1:1) and allowed to be kept quiet for 3 hours, followed by extracting lipids with the above-indicated mixed solvent from an area of 5 cm$^2$.

The extracted liquids were transferred to a weighting bottle, from which the solvent was removed to a constant weight, followed by measuring a weight of the lipids by the use of an ultramicro balance. The results are shown in Table 1 below, from which it will be seen that the cholesteryl ester of the invention significantly increased the amount of secretion of sebum.

TABLE 1

|  | Increment at Applied Site*1 ($\mu g/cm^2/3$ hrs) | |
|---|---|---|
|  | Prior to Application | After 2 Weeks |
| Cholesteryl methyl-branched isostearate-containing cream (Ex. 1) | 0.0 ± 40.2 | 29.9 ± 29.3*2 |
| 5% γ-oryzanol-containing cream (using vaseline as substrate) | 0.0 ± 43.3 | 18.3 ± 38.7 |

*1: Calculation of the increment of the sebum secretion $$\text{Increment} = \frac{\begin{array}{c}\text{Amount of sebum}\\\text{secretion from the}\\\text{skin applied with}\\\text{the cholesteryl}\\\text{ester-containing}\\\text{cream}\end{array} - \begin{array}{c}\text{Amount of sebum}\\\text{secretion from the}\\\text{skin applied with}\\\text{a cream free of the}\\\text{cholesteryl ester}\end{array}}{5}$$

*2: $P < 0.05$ (significant probability)

Experimental Example 2

[Influence of Cholesteryl Ester of Branched Fatty Acid on Sebum Secretion and Sebaceous Gland]

The cholesteryl methyl-branched isostearate as used in Experimental Example 1 was applied, as it is, to the skin on the back of rats every day over 10 days. For comparison, 5% γ-oryzanol-containing vaseline was also applied in the same manner as stated above.

The measurement of the amount of sebum secretion at the applied region was effected in the same manner as in Experimental Example 1. The measurement of an amount of sebum secretion one hour after defatting revealed that the region where the cholesteryl ester of the invention was applied was significantly accelerated in sebum secretion as compared with a control rat group in which only hair was cut. The results are shown in Table 2.

It was also recognized histologically that the rat group which was applied with the cholesteryl ester of the invention had enlarged sebaceous gland, and thus the ester was found to have the sebaceous gland-activating action.

TABLE 2

|  | Amount of Sebum Secretion Relative Value *4 | Area of Sebaceous Grand *3 Relative Value *5 |
|---|---|---|
| Rats treated with cholesteryl methyl-branched isostearate | 178.0 ± 25 | 139.5 ± 50.2 |
| Rats treated with 5% γ-oryzanol (vaseline base) | 101.1 ± 34.6 | 110.4 ± 44.6 |
| Non-treated rats (control) | 100 ± 15.7 | 100 ± 49.8 |

*3 Sectional area of the sebaceous gland in HE preparation.
*4 Significant over the control at $P < 0.05$.
*5 Significant over the control at $P < 0.0001$.

Experimental Example 3

Cholesteryl esters of branched fatty acids having different types of fatty acid moieties were used to determine the influence thereof on the sebaceous gland. For comparison, cholesteryl esters of linear fatty acids and cholesteryl esters of branched fatty acids at low concentrations were also used to determine their effect on the sebum secretion.

Each cholesteryl ester being tested was mixed with vaseline at a concentration of 50% and was applied every day over 2 weeks on the skin on the back of hair-cut rats. After the two weeks, the amount of sebum secretion at the applied place was measured in the same manner as in Experimental Example 1, revealing that all the esters served to accelerate the sebum secretion. Among the tested cholesteryl ester derivatives, the esters of the linear fatty acids such as cholesteryl linoleate, cholesteryl oleate and the like were found to be very low in the accelerating effect. Moreover, when the cholesteryl methyl-branched isostearate was used at low concentrations of 1% and 5%, the effect of accelerating the sebum secretion was not satisfactorily developed. The results are shown in Table 3.

TABLE 3

| Compounds | Concentration | Amount of Sebum Secretion (Relative Value) |
|---|---|---|
| Invention Product |  |  |
| Cholesteryl methyl-branched isostearate | 50 | 210.0 ± 22.8* |
| Cholesteryl 5,7,7-trimethyl-2-(1,3,3-trimethylbutyl)-octanoate | 50 | 383.0 ± 8.4** |
| Cholesteryl 2-heptylundecanoate | 50 | 262.9 ± 27.1* |
| Cholesteryl 2-hexyldecanoate | 50 | 212.1 ± 54.0* |
| Cholesteryl 2-octyldodecanoate | 50 | 227.1 ± 67.8* |
| Cholesteryl 2-pentylnonanoate | 50 | 255.0 ± 83.7* |
| Comparison |  |  |
| Cholesteryl linoleate | 50 | 120.4 ± 25.4 |
| Cholesteryl oleate | 50 | 135.5 ± 29.5 |
| Cholesteryl methyl-branched isostearate (5%) | 5 | 123.8 ± 42.6 |
| Cholesteryl methyl-branched isostearate (1%) | 1 | 117.8 ± 41.3 |
| Vaseline | — | 111.8 ± 18.0 |
| Control |  |  |
| Non-treated | — | 100.0 ± 5.7 |

*$P < 0.05$ Student's t-test
**$P < 0.01$

EXAMPLE 1

| (Composition) |  |
|---|---|
| Monocetyl phosphate | 1.0 (wt %) |
| Oleophilic glycerine monostearate | 2.5 |
| 2-Octyldodecyl myristate | 30.0 |
| Butylparaben | 0.1 |
| Methylparaben | 0.1 |
| Propylene glycol | 6.0 |
| L-arginine | 0.5 |
| Cholesteryl methyl-branched isostearate | 30.0 |
| Water | balance |

(Preparation)

The composition of the above formulation was mixed to obtain a cream in the form of an O/W-type emulsion. When the cream was applied to the skin on the cheek of women suffering from chapped skin once a day over 2 weeks, the cheek skin became smooth.

EXAMPLE 2

Hydrophilic Ointment of sebum Secretion Accelerator:

| (Composition) | |
| --- | --- |
| Self-emulsifying glycerine monostearate | 1.5 (wt %) |
| Oleophilic glycerine monostearate | 2.0 |
| Cetyl alcohol | 4.0 |
| Vaseline | 4.0 |
| Squalane | 7.0 |
| Cholesteryl methyl-branched isostearate | 30.0 |
| Glycerine | 5.0 |
| Methylparaben | 0.1 |
| Butylparaben | 0.1 |
| Water | balance |
| | 100 |

(Preparation)

The composition of the above formulation was mixed to prepare a hydrophilic ointment. This ointment was applied to the human chapped skin once a day over 2 weeks. As a result, it was found that the chapped place was improved.

EXAMPLE 3

Oily Ointment of Sebum Secretion Accelerator:

| (Composition) | |
| --- | --- |
| Vaseline | 35.0 (wt %) |
| Liquid paraffin | 10.0 |
| Cholesteryl methyl-branched isostearate | 55.0 |

(Preparation)

The composition of the above formulation was mixed to obtain an oily ointment. This ointment was applied to the human chapped skin in the same manner as in Example 2, with the skin becoming smooth.

What is claimed is:

1. A method for accelerating sebum secretion in a human being comprising applying to the skin of a human being in need of accelerated sebum secretion a composition comprising a cholesteryl ester of a branched fatty acid represented by the general formula

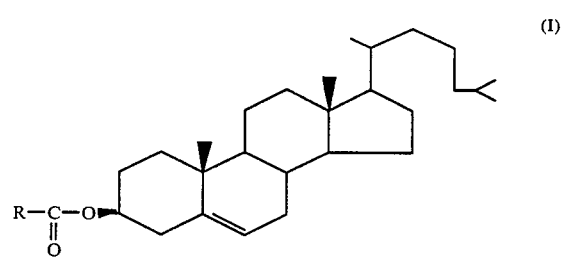

in which R represents a saturated branched aliphatic hydrocarbon group having from 11 to 23 carbon atoms and the branching comprises at least one alkyl substituent at a position between the carboxyl bond and the center of the main chain, in an amount not smaller than 25 wt. % of the total composition.

2. The method of claim 1, wherein said ester is cholesteryl methyl-isostearate.

3. The method of claim 1, wherein the ester is cholesteryl 5,7,7-trimethyl-2-(1,3,3-trimethylbutyl) octanoate.

4. The method of claim 1, wherein the ester is cholesteryl 2-heptylundecanoate.

5. The method of claim 1, wherein the ester is cholesteryl 2-hexyldecanoate.

6. The method of claim 1, wherein the ester is cholesteryl 2-octyldodecanoate.

7. The method of claim 1, wherein the ester is cholesteryl 2-pentylnonanoate.

8. The method of claim 1, wherein the composition comprises 30 wt % or more of said cholesteryl ester.

9. The method of claim 1, wherein the composition comprises 50 wt % or more of said cholesteryl ester.